United States Patent [19]

Counsell et al.

[11] Patent Number: 4,883,649
[45] Date of Patent: Nov. 28, 1989

[54] IODINATED CLONIDINE DERIVATIVES AS RADIOACTIVE IMAGING TRACERS

[75] Inventors: Raymond E. Counsell; Marcian Van Dort; Richard Neubig, all of Ann Arbor, Mich.

[73] Assignee: The University of Michigan, Ann Arbor, Mich.

[21] Appl. No.: 257,181

[22] Filed: Oct. 13, 1988

Related U.S. Application Data

[63] Continuation of Ser. No. 774,260, Sep. 10, 1985, abandoned.

[51] Int. Cl.[4] .................... A61K 43/00; C07D 403/30
[52] U.S. Cl. ...................................... 424/1.1; 548/315
[58] Field of Search ........................ 548/315; 424/1.1

[56] References Cited

U.S. PATENT DOCUMENTS 4,262,005 4/1981 McCarthy et al. ................. 548/315

Primary Examiner—Mary C. Lee
Assistant Examiner—Robert C. Whittenbaugh
Attorney, Agent, or Firm—Rohm & Monsanto

[57] ABSTRACT

Iodinated clonidine derivatives useful, inter alia, as a probe for identification and characterization of $\alpha_2$-adrenergic receptor sites and as tracers for imaging techniques such as positron emission tomography or computer assisted tomography. Binding competition studies have indicated that p-iodoclonidine, for example, is a particularly efficacious binder for $\alpha_2$-adrenergic sites.

20 Claims, 3 Drawing Sheets

IODINATED CLONIDINE DERIVATIVES AS RADIOACTIVE IMAGING TRACERS

This invention was made with Government support under Contract No. CA-08349 awarded by the Department of Health and Human Services. The Government has certain rights in this invention.

This application is a continuation of application Ser. No. 774,260, filed Sept. 10, 1985 now abandoned.

BACKGROUND OF THE INVENTION

This invention relates to analogs of clonidine, and more particularly to a novel iodinated clonidine derivatives, such as p-iodoclonidine, which in its radioactive form, for example, is useful as a probe for the identification and characterization of $\alpha_2$-adrenergic receptor sites.

Clonidine has the chemical formula:

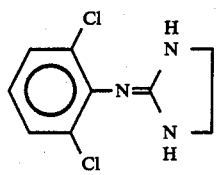

It is also known by its chemical name 2-(2,6-dichlorophenylamine)-2-imidazoline. Clonidine is known to be site-specific in that it binds preferentially to $\alpha_2$-adrenergic receptor sites. Clonidine activates the $\alpha_2$-receptor sites to produce a response similar to norepinephrine in the central nervous system.

Commercially available analogs of clonidine, such as $^3$H-clonidine or $^3$H-p-aminoclonidine, are radio-tagged with tritium ($^3$H) and used as probes for in vitro research on $\alpha_2$-adrenergic receptor sites. While such tagging does yield radio-emissive compounds, the emission is strictly of the weak beta-type, so that any interfering structure, such as nearby tissue in vivo, may completely absorb, or substantially mask, the emission before the tritium can be detected. Therefore, beta-measuring instruments must be very sensitive and intervening tissue absorption must be factored in, thereby increasing the problems created by the use of beta-emissive radio-tagged clonidine in a laboratory situation. Thus, a radio-tagged form of clonidine having a stronger emissive character would be of substantial benefit to an investigator of the pharmacological actions of clonidine at the molecular level.

Another commercially available clonidine derivative is clonidine hydrochloride which is used as an antihypertensive drug to alleviate high blood pressure. Laboratory studies have indicated that the drug and its metabolites leave the patient primarily through urinary discharge. Naturally, extensive laboratory testing has been required to show efficacy and safety of this drug. Early laboratory studies of clonidine hydrochloride in rats indicated that significant buildup of clonidine occurs in the choroid of the eye, with the possibility of retinal degeneration. Accordingly, radio-tagged clonidine would be a valuable tool for testing clonidine site specificity, build-up rates, and metabolic departure from tissues. Moreover, when clonidine is used as an antihypertensive, it initially stimulates peripheral $\alpha$-adrenergic receptors, thereby producing transient vasoconstriction. Inhibition of bulbar sympathetic cardioaccelerator and sympathetic vasoconstrictor centers causes a decrease in sympathetic outflow from the brain. The binding capacity of clonidine renders it useful as a probe for the study of central nervous system-depressant effects of clonidine hydrochloride.

Advances in non-invasive imaging techniques, such as positron emission tomography, or brain scanning by computer assisted tomography, required equivalent advances in tracers which will be readily detected, have a residence time in the body sufficient to permit testing but not so long as to create undesired side effects, will be site specific so that low dosage levels are adequate, and will be non-toxic. There is, thus, a need for an improved tracer for neurological, or physiological, research and disorder diagnosis.

It is, therefore, an object of the invention to provide a novel clonidine compound which is $\alpha_2$-adrenergic receptor site specific.

It is another object of the invention to provide a novel clonidine compound which binds $\alpha_2$-adrenergic receptors better than currently used clonidine compounds.

It is a further object of the invention to provide a new radioactive clonidine compound which binds $\alpha_2$-adrenergic receptors with greater site specificity than currently used tritium clonidine compounds.

It is also an object of the invention to provide a strong gamma-emissive radio-tagged tracer for $\alpha_2$-adrenergic receptors.

It is an additional object of the invention to provide an improved tracer for neurological research on the central nervous system.

It is still another object of the invention to provide an improved tracer for diagnosis of neurological or physiological disorders by such imaging techniques as positron emission tomography, computer assisted tomography, or myocardial imaging.

It is yet an additional object of the invention to provide a tracer which is physiologically acceptable and non-toxic and which has appropriate residence time in the human body.

It is additionally an object of the invention to provide methods of preparation for iodinated clonidine compounds and radio-tagged iodinated clonidine compounds.

SUMMARY OF THE INVENTION

The foregoing and other objects are achieved by this invention which provides novel clonidine derivatives, and salts thereof, having the formula:

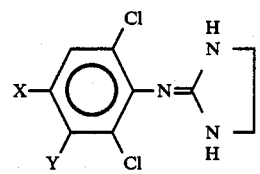

wherein X is iodine or amino ($NH_2$). In embodiments where X is $NH_2$, Y is iodine. In other embodiments where X is iodine, Y is hydrogen.

In a preferred embodiment of the invention, radioactive iodine (e.g., $^{122}$I, $^{123}$I, $^{125}$I, $^{131}$I) is substituted for the stable iodine.

In specific illustrative embodiments, the novel derivatives are p-iodoclonidine and an iodinated p-aminoclonidine derivative.

In other embodiments of the invention, the clonidine derivative can be provided as a salt, such as the hydrochloride, chloride, citrate, tartrate, sulfate or bromide salt.

DETAILED DESCRIPTION OF THE INVENTION

Figure 1:
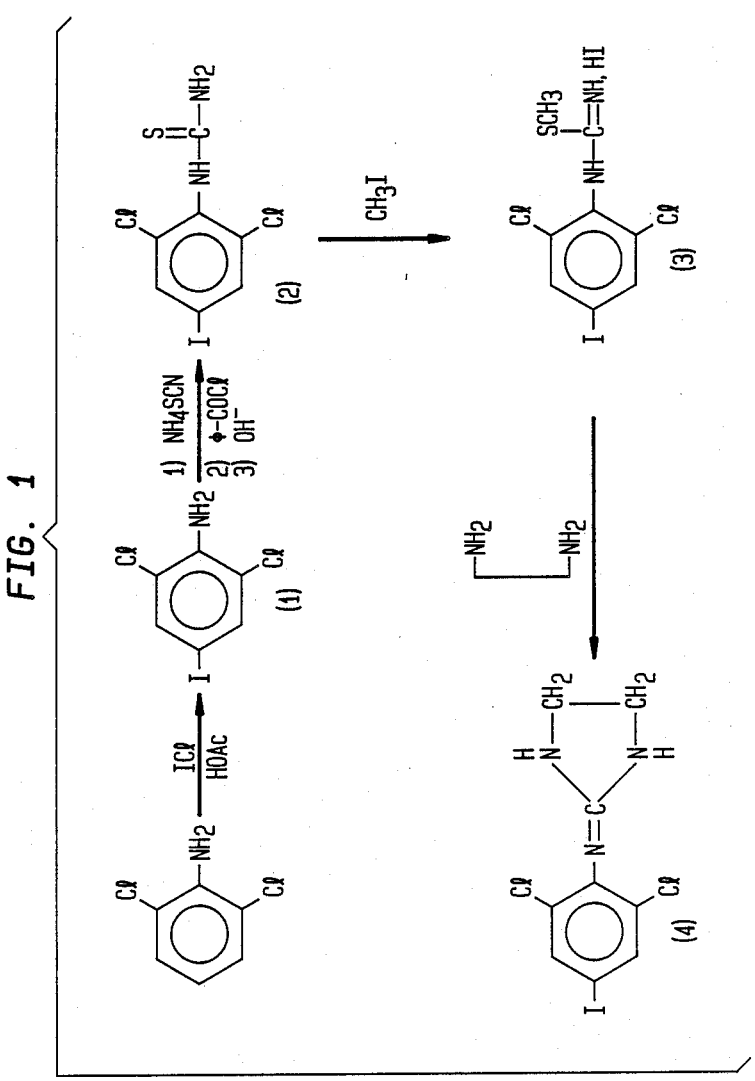
FIG. 1 is a flow chart of a reaction scheme for producing p-iodoclonidine.

FIG. 1 shows a flow chart of an illustrative preparational technique for p-iodoclonidine.

Referring to FIG. 1, the prepartion of Compound (1), 2,6,-dichloro-4-iodoaniline, is as follows:

A solution of 5.06 g iodine monochloride (31.20 mmol) in 20 ml of glacial acetic acid was added dropwise to a vigorously stirred solution of 5.05 g (31.20 mmol) 2,6-dichloroaniline in 40 ml of glacial acetic acid. The reaction mixture was stirred for 1 hour at room temperature after the reaction was complete. Following dilution with 400 ml $H_2O$, the product was filtered and washed with 100 ml of 10% aq. sodium bisulfite solution. The crude product was recrystallized from methanol/water (1:1 by vol.)to give 7.54 g of Compound (1) (yield: 84%).

A vigorously stirred hot solution of 1.18 g (15.48 mmol) anhydrous ammonium thiocyanate in 30 ml of dry acetone was treated dropwise with 1.82 g (12.90 mmol) of benzoyl chloride. The reaction mixture was refluxed 5 minutes and then subjected to dropwise addition of a solution of 3.71 g (12.90 mmol) of Compound (1) in 40 ml of dry acetone. After an hour of heating the mixture, the volume was reduced, in vacuo, to half. 400 ml of $H_2O$ was added to dilute the mixture and the mixture was refrigerated. The crude product thus obtained was filtered, dried, and used without further purification in the next step.

This crude product was heated to reflux with 20 ml of 10% aqueous sodium hydroxide solution for 10 minutes. The reaction mixture was cooled prior to treatment with concentrated HCl until it was sufficiently acidic to precipitate both benzoic acid and 2,6-dichloro-4-iodophenylthiourea. It was then made basic with concentrated $NH_4OH$ to a pH of 9 to dissolve the benzoic acid. The product was filtered and recrystallized from 100 ml of 95% aqueous ethanol to afford 3.65 g of Compound (2), 1-benzoyl-3-(2,6-dichloro-4-iodophenyl)-thiourea (yield: 81.5%, based on Compound (1)).

A solution of 1,25 g (3.60 mmol) of Compound (2), prepared above, in 10 ml of freshly distilled dry methanol, was treated with 0.51 g (3.60 mmol) methyl iodide. The solution was refluxed for 2 hours, cooled, and placed in a vacuum to evaporate. The crystalline product was washed with several portions of diethyl ether and dried to afford 1.72 g of Compound (3), N-(2,6-dichloro-4-iodophenyl)-S-methylisothiourea (yield: 98%).

A mixture of 1.0 g (2.04 mmol) Compound (3), 0.41 g (6.13 mmol) ethylenediamine, and 3 ml absolute ethanol was heated with stirring in a steel bomb at 140° C. to 150° C. for 18 hours. The oily residue was solubilized in 2 ml ethanol and treated with 5 ml of 50% aqueous KOH. Extraction of the alkaline solution with diethyl ether four times (50 ml apiece), followed by drying with $MgSO_4$, and evaporation in vacuo afforded a pale yellow oil.

Separation of the two major products was achieved by column chromatography on silica gel eluted with diethyl ether. The fraction containing the less polar component yielded an unidentified product upon evaporation of the solvent. The alkaline solution, obtained as a yellow oil, was converted to the hydrochloride salt by dissolution in 1 ml of absolute ethanol and treatment with ethereal HCl.

The end result of the technique of FIG. 1 was Compound (4), 2-(2,6-dichloro-4-iodophenylimino-2)imidazolidine.

Figure 2:
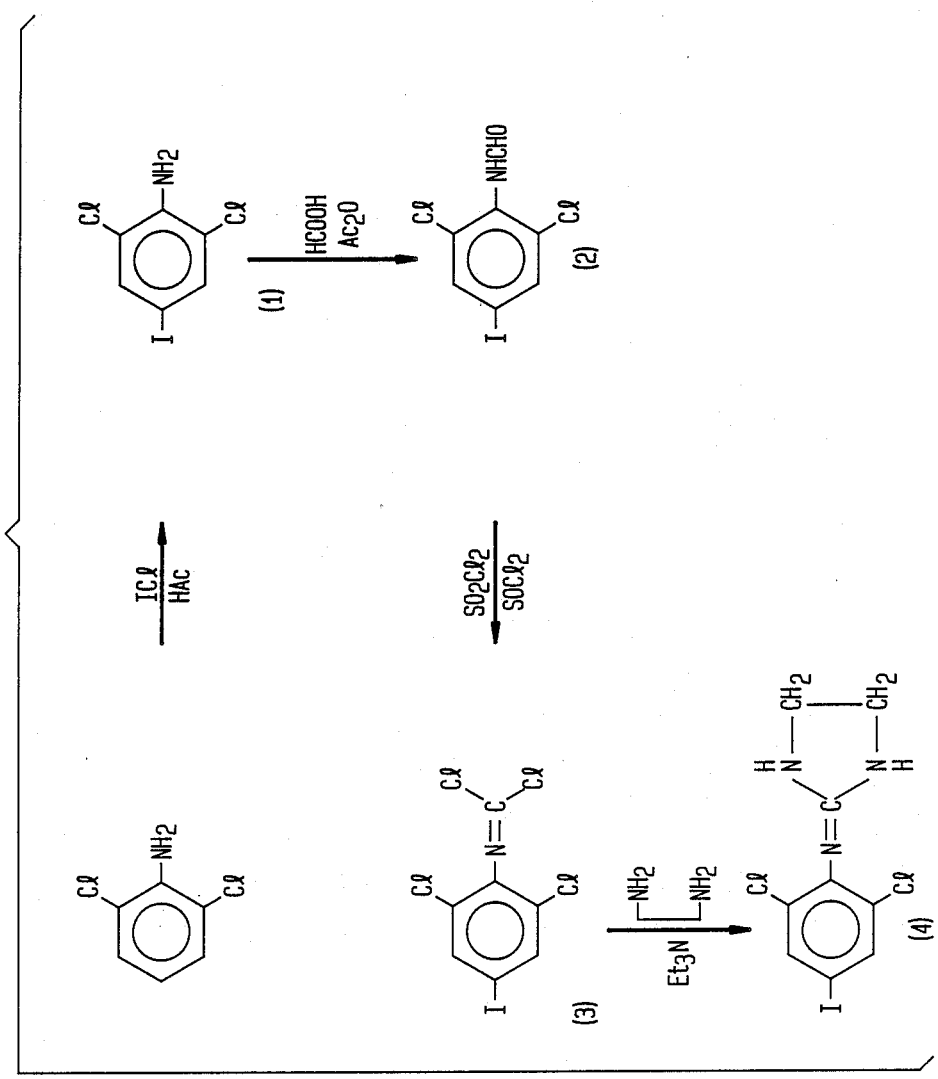
FIG. 2 is a flow chart of an alternative reaction scheme for producing p-iodoclonidine.

FIG. 2 shows a flow chart of another illustrative example of a preparatory scheme of p-iodoclonidine.

Figure 3:
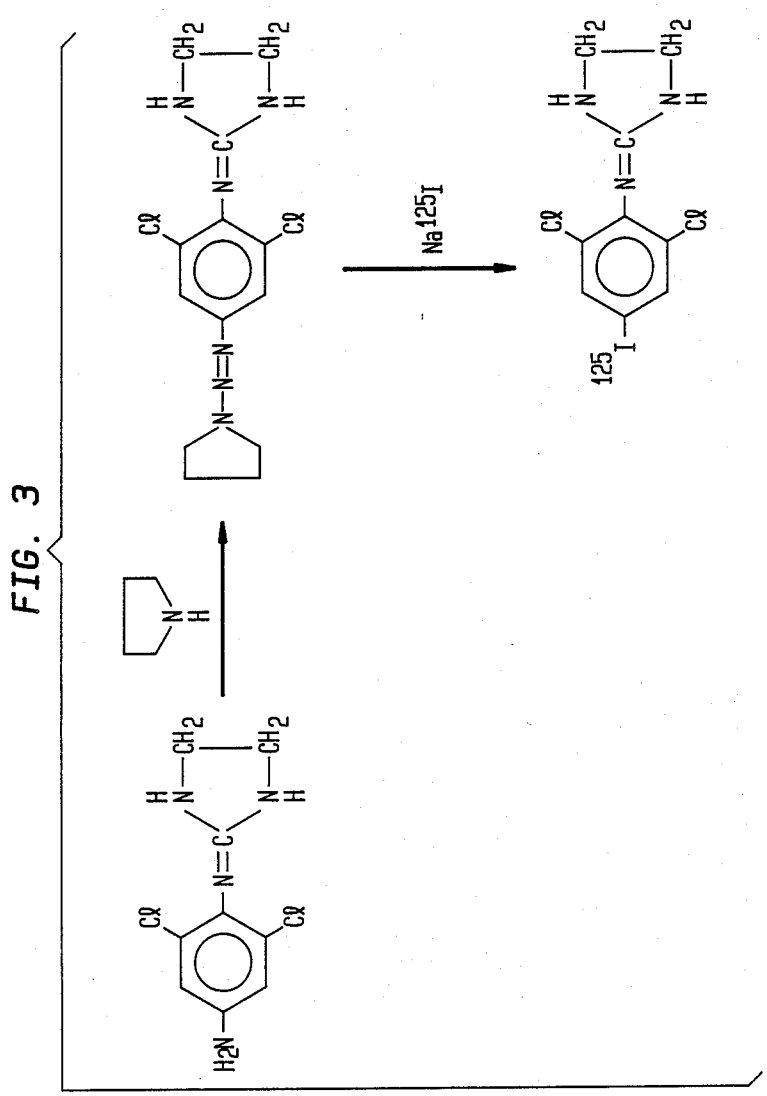
FIG. 3 is a flow chart for producing a radio-tagged p-iodoclonidine.

FIG. 3 shows yet another illustrative example of a preparatory scheme for p-iodoclonidine which is characterized by the production of a novel, highly reactive intermediate. This intermediate is labeled Compound (1) on FIG. 3 and has the chemical name 2-(2,6-dichloro-4-(3,3-(1,4-butanediyl)triazeno)phenylimino-2)imidazoline. This intermediate is formed by the diazotization of p-aminoclonidine, followed by treatment of the diazonium salt with pyrrolidine. The advantage of the scheme of FIG. 3 is that the triazeno group is readily replaced with iodine, or radioactive iodine. Higher specific radioactivity is achievable through use of this scheme.

p-Aminoclonidine, or 2-(2,6-dichloro-4-aminophenylimino-2)imadazoline, is available commercially from Sigma Chemical Company, St. Louis, Mo., or it can be synthesized in the laboratory.

A solution of 150 mg p-aminoclonidine (0.61 mmol) in 0.13 ml (2.4 mmol) of concentrated sulfuric acid and 0.26 ml of $H_2O$ was maintained at 0° C. by cooling in an ice bath. A cold (0° C.) solution of 46 mg (0.67 mmol) sodium nitrite in 0.3 ml $H_2O$ was added dropwise with stirring. The temperature was maintained between 0° C. and 5° C. during the addition which took approximately 10 minutes. Stirring was continued for an additional 15 minutes at ice-bath temperature, and the reaction mixture was treated dropwise with a cold solution (0° C.) of 0.056 ml (0.67 mmol) of pyrrolidine in 5 ml of aq. 1 M potassium hydroxide. After stirring for an additional 15 minutes at room temperature, the reaction mixture was extracted with benzene (four times, 25 ml apiece). The combined benzene layers were dried over $MgSO_5$ and the solvent was evaporated. The crude product was flash chromatographed on silica gel with the solvent system of chloroform:ethanol:conc. ammonium hydroxide (4:2:1:0.1). The purified material was recrystallized from 1:1 methylene chloride/hexane to yield 146 mg (73%) Compound (1).

Compound (1) can be reacted with NaI or $Na^{125}I$ in in trifluoroacetic acid, for example, to obtain stable or radioiodinated p-iodoclonidine, Compound (2) on FIG. 3.

Radioiodination of p-iodoclonidine can be accomplished by a variety of techniques, some of which are known in the art, such as by exchange of a leaving group (the triazene on the intermediate Compound (1) of FIG. 3) or isotope exchange reactions.

In a preferred embodiment of the invention, an isotope exchange-type technique is utilized wherein the substrate and radioiodide are reacted at an elevated temperature in a "melt". The molten reaction medium possesses a sufficiently high dielectric constant to solubilize both the substrate and the radioiodide. Examples of reaction media currently in use are benzoic acid and acetamide. In a specific preferred embodiment, an acidic exchange medium comprising pivalic acid (mp 33° C., bp 164° C.), a homolog of acetic acid known as trimethyl acetic acid, is used.

A solution of 1 mg p-iodoclonidine, 300 ml tetrahydrofuran (THF) and 50 ml Na$^{125}$I (specific activity of 2.0 mCi) was placed in a vial. The vial was sealed, and the solvent was evaporated under a stream of N$_2$. 25 mg Pivalic acid were then added, the vial was resealed, and heated to about 155° C. for 2 hours in an oil bath. The vial was cooled and the contents were diluted with 800 l THF and chromatographed on silica gel eluted with ethyl acetate. Radiochemical purity was established using radiochromatography of untagged p-iodoclonidine as a standard. This procedure yielded 80% radiotagged p-iodoclonidine with a specific activity of 0.32 Ci/mmol.

The $^{125}$I radioiodinated compound is advantageous for in vitro work due to the longer half life of $^{125}$I as compared to other iodine isotopes. Such a compound would have applicability in binding assays of $\alpha_2$-adrenergic receptor sites. Of course, radio-tagging can be accomplished with $^{123}$I or $^{131}$I, for example, and indeed, these isotopes would be preferred for in vivo applications such as tracers for brain scanning. For positron emission tomography, the positron-emitting $^{122}$I isotope is preferred. Clonidine is known to localize in the heart, and thus, a radio-tagged clonidine derivative of the type discribed herein may be used in myocardial imaging.

Given below are the results of studies conducted showing drug competition for adrenergic binding sites in human platelet membranes. p-Iodoclonidine has a greater affinity for the receptor than clonidine. It is, therefore, possible that the non-radioactive p-iodoclonidine, or related derivatives, have therapeutic value.

Human platelet plasma membranes were prepared by sonication of human platelet concentrates (Red Cross) followed by centrifugation on a discontinuous sucrose gradient (14%/34% by weight) for 3 hours at 140,000 x g. The membrane fraction was collected from the interface of the heavy and light sucrose, and will be herein designated as purified platelet plasma membrane (PPM).

Binding of $^3$H-p-aminoclonidine to PPM was measured by incubation of 3 nmol $^3$H-p-aminoclonidine with PPM (0.1 to 0.2 mmol protein) in 1.0 ml of a buffer containing 50 mmol Tris-Hydrochloride, 10 mmol Magnesium chloride, 1 mmol EDTA at pH 7.6 for 30 minutes at 23° C. The amount of $^3$H-p-aminoclonidine bound at the end of this time was measured by collecting the PPM on a Whatman GF/C glass fiber filter followed by washing away non-bound $^3$H-p-aminoclonidine by two washes of 10 ml each of buffer. Bound radioactivity was measured by scintillation counting of the GF/C filter in OCF scintillation cocktail (Amerscham) on a Beckman LR 8100 scintillation counter. The ability of nonradioiodinated clonidine to compete for the $\alpha_2$-adrenergic receptor binding sites was expressed as the percentage bound in the presence of added compound. Non-specific binding of the $^3$H-p-aminoclonidine was measured in the presence of 10 mmol oxymetazylene hydrochloride. The target compound p-iodoclonidine was more potent than either p-aminoclonidine or clonidine in competition for $\alpha_2$-adrenergic receptor sites.

Table I shows the IC$_{50}$ for a number of compounds for competition with $^3$H-p-aminoclonidine in binding to platelet $_2$-adrenergic receptor sites. IC$_{50}$ is the concentration of compound which reduces binding to 50% of the initial value. As can be seen, p-iodoclonidine is more potent (IC$_{50}$=1.3) than clonidine, p-aminoclonidine, or yohimbine, the most commonly used probes for adrenergic receptors. Moreover, p-iodoclonidine binds better than epinephrine, a natural adrenergic binding agent.

TABLE I

| DRUG | IC$_{50}$ (nM) |
| --- | --- |
| Yohimbine | 8.0 |
| Epinephrine | 8.0 |
| Clonidine | 21.0 |
| p-Aminoclonidine | 4.0 |
| p-Iodoclonidine | 1.3 |

Another active compound is an iodinated clonidine derivative of p-aminoclonidine. This compound is 2-(2,6-dichloro-3-iodo-4-aminophenylimino-2)imadazoline. Methods can be devised for iodinating p-aminoclonidine by those of skill in the art.

Although the invention has been described in terms of specific embodiments and applications, persons skilled in the art can, in light of this teaching, generate additional embodiments for the applications disclosed herein, and for other applications, without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A compound, and the salts thereof, of the formula:

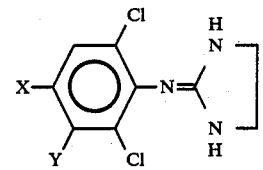

wherein X is selected from the group consisting of radioactive isotopes of iodine and NH2 and Y is H or, when X is NH2, Y is selected from the group consisting of iodine and radioactive isotopes of iodine.

2. The compound of claim 1 wherein X is a radioactive isotope of iodine and Y is H, the compound being 2-(2,6-dichloro-4-iodophenylimino-2)imadazoline.

3. The compound of claim 1 which is 2-(2,6-dichloro-3-iodo-4-aminophenylimino-2)imadazoline.

4. The compound of claim 1 wherein said salts are selected from the group consisting of hydrochloride, tartrate, citrate, sulfate, chloride and bromide.

5. The compound of claim 1 wherein said radioactive isotope of iodine is selected from the group consisting of $^{122}$I, $^{123}$I, $^{125}$I, and $^{131}$I.

6. A site-specific radioactive tracer compound having the formula:

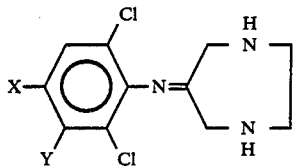

wherein X is selected from the group consisting of radioactive isotopes of iodine and NH₂ and Y is H or, when X is NH₂, Y is a radioactive isotope of iodine.

7. The site-specific radioactive tracer compound of claim 6 wherein X is a radioactive isotope of iodine and Y is H, the compound being 2-(2,6-dichloro-4-iodophenylimino-2)imadazoline.

8. The site-specific radioactive tracer compound of claim 7 wherein X is NH₂ and Y is selected from the group consisting of iodine and radioactive isotopes of iodine, the compound being 2-(2,6-dichloro-3-iodo-4-aminophenylimino-2)imadazoline.

9. The site-specific radioactive tracer compound of claim 6 wherein said radioactive isotope of iodine is selected from the group consisting of ¹²²I, ¹²³I, ¹²⁵I, and ¹³¹I.

10. A method of radioimaging comprising:
administering to the body of a living being an effective amount of a radioactive tracer compound as claimed in claim 6.

11. A radioactive binding assay composition for a₂-adrenergic receptor sites, said assay composition comprising a compound of the formula:

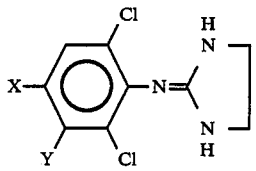

wherein X is selected from the group consisting of radioactive isotopes of iodine and NH₂ and Y is H or, when X is NH₂, Y is a radioactive isotope of iodine.

12. The radioactive binding assay composition of claim 12 wherein the radioactive isotope of iodine is ¹²⁵I.

13. The compound of claim 1 wherein said radioactive isotope of iodine is selected from the group consisting of 122I, 123I, 125I, and 131I.

14. A site-specific radioactive tracer compound having the formula:

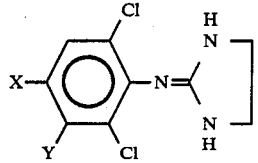

wherein X is selected from the group consisting of radioactive isotopes of iodine and NH2 and Y is H or, when X is NH2, Y is a radioactive isotope of iodine.

15. The site-specific radioactive tracer compound of claim 14 wherein X is a radioactive isotope of iodine and Y is H, the compound being 2-(2,6-dichloro-4-iodophenylimino-2)imadazoline.

16. The site-specific radioactive tracer compound of claim 14 wherein X is NH2 and Y is selected from the group consisting of iodine and radioactive isotopes of iodine, the compound being 2-(2,6-dichloro-3-iodo-4-aminophenylimino-2)imadazoline.

17. The site-specific radioactive tracer compound of claim 14 wherein said radioactive isotope of iodine is selected from the group consisting of 122I, 123I, 125I, and 131I.

18. A method of radioimaging comprising:
administering to the body of a living being an effective amount of a radioactive tracer compound as claimed in claim 14.

19. A radioactive binding assay composition for 2-adrenergic receptor sites, said assay composition comprising an effective amount of the compound of the formula:

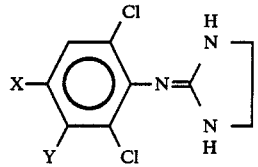

wherein X is selected from the group consisting of radioactive isotopes of iodine and NH2 and Y is H or, when X is NH2, Y is a radioactive isotope of iodine.

20. The radioactive binding assay composition of claim 19 wherein the radioactive isotope of iodine is 125I.

* * * * *